(12) United States Patent
Chen et al.

(10) Patent No.: US 7,419,964 B2
(45) Date of Patent: Sep. 2, 2008

(54) TREATMENT OF HSV-RELATED PATHOLOGIES USING SSDNA

(75) Inventors: Yin Chen, Pearland, TX (US); Malcolm Skolnick, Houston, TX (US)

(73) Assignee: Cytogenix, inc., Houston, TX (US)

( * ) Notice: Subject to any disclaimer, the term of this patent is extended or adjusted under 35 U.S.C. 154(b) by 691 days.

(21) Appl. No.: 10/313,828

(22) Filed: Dec. 6, 2002

(65) Prior Publication Data

US 2004/0235763 A1    Nov. 25, 2004

Related U.S. Application Data

(63) Continuation-in-part of application No. 10/136,218, filed on May 1, 2002, now abandoned, and a continuation-in-part of application No. 09/397,782, filed on Sep. 16, 1999, now abandoned.

(51) Int. Cl.
| | |
|---|---|
| A01N 43/04 | (2006.01) |
| C12Q 1/68 | (2006.01) |
| C12N 15/00 | (2006.01) |
| C07H 21/02 | (2006.01) |
| C07H 21/04 | (2006.01) |

(52) U.S. Cl. ............................ 514/44; 435/6; 435/91.1; 435/320.1; 435/455; 514/1; 536/23.1

(58) Field of Classification Search ...................... 435/6, 435/91.1, 320.1, 91.31, 455, 458; 536/23.1, 536/24.5, 24.32; 514/1, 2, 44
See application file for complete search history.

(56) References Cited

U.S. PATENT DOCUMENTS

| | | | |
|---|---|---|---|
| 5,436,141 | A | 7/1995 | Miyata et al. |
| 5,503,978 | A | 4/1996 | Schneider et al. |
| 5,795,721 | A | 8/1998 | Rabin et al. |
| 5,837,289 | A | 11/1998 | Grasela et al. |
| 6,057,367 | A | 5/2000 | Stamler et al. |
| 6,190,866 | B1 | 2/2001 | Nielsen et al. |

FOREIGN PATENT DOCUMENTS

| | | |
|---|---|---|
| EP | A2-0530112 | 3/1993 |
| EP | A2-0532380 | 3/1993 |
| EP | A2-0562206 | 9/1993 |
| WO | WO-A-94/01550 | 1/1994 |
| WO | WO-A-94/13689 | 6/1994 |
| WO | WO-A-94/20639 | 9/1994 |
| WO | WO-A-94/23026 | 10/1994 |
| WO | WO-A-95/35369 | 12/1995 |
| WO | WO 00/22113 | 4/2000 |
| WO | WO 00/22114 | 4/2000 |
| WO | WO 01/25419 | 4/2001 |
| WO | WO 03/093424 | 11/2003 |

OTHER PUBLICATIONS

Peracchi, A. et al., Rev. Med. Virol., vol. 14, pp. 47-64 (2004).*
Crooke, S. Antisense Research and Application, Chapter 1, pp. 1-50, Ed. by S. Crooke, Publ. by Springer-Verlag (1998).*
Branch, A., Trends in Biochem. Sci., vol. 23, pp. 45-50 (1998).*
Chirila, T. et al., Biomaterials, vol. 23, pp. 321-342 (2002).*
Agrawal, S. et al., Molecular Med. Today, vol. 6, pp. 72-81 (2000).*
Crooke, S., et al., Antisense Research and Application, Chapter 1, 1-50, Ed. by S. Crooke, Springer-Verlag, 1998.
Agrawal, S., et al., *Antisense therapeutics: is it as simple as complementary base recognition?*, Molecular Medicine Today, 6:72-81, 2000.
Akhtar, S., et al., *The delivery of antisense therapeutics*, Advanced Drug Delivery Reviews, 44:3-21, 2000.
Alexander, C., et al., *Bacterial lipopolysaccharides and innate immunity*, J. of Endotoxin Research, 7(3): 167-202, 2001.
Angus, D., et al., *Epidemiology of severe sepsis in the United States: Analysis of incidence, outcome, and associated costs of care*, Crit Care Med., 29(7):1303-1310, 2001.
Beard, P., et al., *Herpes simplex virus immediate early infected-cell polypeptide 4 binds to DNA and promotes transcription*, Proc. Natl. Acad. Sci., 83:4016-4020, 1986.
Bochud, P., et al., *Antibiotics in sepsis*, Intensive Care Med., 27: S33-S48, 2001.
Branch, Andrea, *A good antisense molecule is hard to find*, Trends in Biochem. Sci., 23:45-50, 1998.
Breaker, R., *Catalytic DNA: in training and seeking employment*, Nature Biotechnology, 17:422-423, 1999.
Breaker, R.R. and Joyce, G.F., *A DNA enzyme that cleaves RNA*, Chemistry & Biology, 1:223-229, 1994.
Breaker, R.R. and Joyce, G.F., *A DNA enzyme with Mg(2+)-dependent RNA phosphodiesterase activity*, Chemistry & Biology, 2: 655-660, 1995.
Breaker, R.R., *Making Catalytic DNAs*, Science, 290: 2095-2096, 2000.
Breaker, R.R., In Vitro *Selection of Catalytic Polynucleotides*, Chem. Rev., 97: 371-90, 1997.
Calandra, T., *Pathogenesis of Septic Shock: Implications for Prevention and Treatment*, Journal of Chemotherapy, 13(1): 173-180, 2001.
Carmi, N., et al., *Cleaving DNA with DNA*, PNAS, 95(5): 2233-2237, 1998.

(Continued)

*Primary Examiner*—Jane Zara
(74) *Attorney, Agent, or Firm*—Cindee R. Ewell (57) ABSTRACT

A composition for treatment of HSV-related pathologies including an expression vector for altering expression of a target sequence in an HSV-infected cell by production of single-stranded cDNA (ssDNA) in the cell in vivo suspended for topical application to an affected site in a suitable delivery vehicle. The expression vector is comprised of a cassette comprising a sequence of interest, an inverted tandem repeat, and a primer binding site 3' to the inverted tandem repeat, and a reverse transcriptase/RNAse H coding gene, and is transfected into the infected cells for inhibition of HSV replication. The resulting ssDNA binds to the target sequence to alter expression of the target sequence for such purposes as gene activation or inactivation using duplex or triplex binding of nucleic acids, site-directed mutagenesis, interruption of cellular function by binding to specific cellular proteins, or interfering with RNA splicing functions.

13 Claims, 3 Drawing Sheets

OTHER PUBLICATIONS

Chen, et al, *In Vivo Expression of Single-Stranded DNA in Mammalian Cells with DNA Enzyme Sequences Targeted to c-raf*, Antisense & Nuc. Acid Drug Development, 10(6): 415-422, Dec. 2000.

Chen, Y., *A novel single-stranded DNA expression vector*, Expert Opin. Biol. Ther., 2(7): 735-740, 2002.

Chen, Y., et al., *Novel Intracellular Single-Stranded DNA Expression System: Production of c-raf RNA-cleaving DNA Enzyme*, Gene Therapy 2001: A Gene Odyssey, Keystone Symposia, Snowbird, Utah, Jan. 2001 (Abstract-1) -Assignee.

Chen, Y., et al., *Novel intracellular single-stranded DNA expression system: Production of c-raf RNA-cleaving DNA enzyme*, Cancer Gene Therapy, vol. 8, Supp. 2, Abs. No. O-6, Dec. 2001 (Abstract-2) -Assignee.

Chirila, T., et al., *The use of synthetic polymers for delivery of therapeutic antisense oligodeoxynucleotides*, Biomaterials, 23:321-342, 2002.

Cohen, J., *The immunopathogenesis of sepsis*, Nature, 420: 885-891, 2002.

Cohen, P., *A Marvel of Biochemical Engineering Means Cells Can Produce DNA Enzymes to Attack Cancer*, New Scientist Oneline News, 1328 GMT, Jan. 9, 2001.

Cuenod, B. and Szostak, J., *A DNA metalloenzyme with DNA ligase activity*, Nature, 375:611-614, 1995.

Dai, K. and Lutkenhaus, J., *ftsZ is an Essential Cell Division Gene in Escherichia coli*, Journal of Bacteriology, 173 (11): 3500-3506, 1991.

Datta, H.J. and Glazer, P.M., *Intracellular generation of single-stranded DNA for chromosomal triplex formation and induced recombination*, Nucleic Acids Research, 29 (24): 5140-5147, 2001.

Deluca, N., et al., *Isolation and Characterization of Deletion Mutants of Herpes Simplex Virus Type 1 in the Gene Encoding Immediate-Early Regulatory Protein ICP4*, Journal of Virology, 56 (2):558-570, 1985.

Dias, Nathalie and Stein, C.A., *Antisense Oligonucleotides: Basic Concepts and Mechanisms*, Molecular Cancer Therapeutics, 1: 347-355, 2002.

Disney, G.H., et al., *The product of varicella-zoster virus gene 62 autoregulates its own promoter*, Journal of General Virology, 71:2999-3003, 1990.

Emilsson et al., *Deoxyribozymes: New Activities and New Applications*, Cellular and Molec Life Sci. 59: 596-607 (2002).

Faulhammer and Famulok, M., *Characterization and Divalent Metalion Dependence of in vitro Selected Deoxyribozymes which Cleave DNA/RNA Chimeric Oligonucleotides*, Jour Molec Biol, 269: 188-203, 1997.

Galocha, B., et al., *The Active Site of ICP47, a Herpes Simplex Virus-encoded Inhibitor of the Major Histocompatibility complex (MHC)-encoded Peptide Transporter Associated with Antigen Processing (TAP), Maps to the NH$_2$—terminal 35 Residues*, J. Exp. Med., 185(9):1565-1572, 1997.

Inouye, S., et al., *Highly Specific Recognition of Primer RNA Structures for 2'-OH Priming Reaction by Bacterial Reverse Transcriptases*, Journal of Biological Chemistry, 274 (44): 31236-31244, 1999.

Jugovic, P., et al., *Inhibition of Major Histocompatibility Complex Class I Antigen Presentation in Pig and Primate Cells by Herpes Simples Virus Type 1 and 2 ICP47*, Journal of Virology, 72(6):5076-5084, 1998.

Lampson, B., et al., *The msDNAs of Bacteria*, Prog. Nucleic Acid Res. Mol. Biol., 67: 65-91, 2001.

Lau, Q.C., et al., *Abrogation of c-RAF expression induces apoptosis in tumor cells*, Oncogene, 16: 1899-1902, 1998.

Li, Y. and Breaker, R., *Phosphorylating DNA with DNA*, Proc. Natl. Acad. Sci., 96:2746-2751, 1999.

Li, Y., et al., *Complete Nucleotide Sequence, Genome Organization, and Biological Properties of Human Immunodeficiency Virus Type 1 in Vivo: Evidence for Limited Defectiveness and complementation*, Journal of Virology, 66(11):6587-6600, 1992.

Mao, J.R., et al., *Gene regulation by antisense DNA produced in vivo*, J. of Biol. Chem., 270(34): 19684-19687, 1995.

Matthews, J.T., et al., *The structure and function of the HSV DNA replication proteins: defining novel antiviral targets*, Antiviral Research, 20:89-114, 1993.

McGeoch, D.J., et al., *Molecular Phylogeny of the Alphaherpesvirinae Subfamily and a Proposed Evolutionary Timescale*, J. Mol. Biol., 238:9-22, 1994.

Mirochnitchenko, O., et al., *Production of single-stranded DNA in mammalian cells by means of a bacterial retron*, J. of Biol. Chem., 269 (4):2380-2383, 1994.

Mohuczy, D., et al., Hypertension, Part 11:354-359, 1999 (first page only).

Moore, T, et al., *Experimental investigation and mathematical modeling of Pluronic F127 gel dissolution: drug release in stirred systems*, Journal of Controlled Release, 67:191-202, 2000.

Moser & Dervan, *Sequence-Specific Cleavage of Double Helical DNA by Triple Helix Formation*, Science, 238: 645-650, 1987.

Nielsen, P., *Peptide nucleic acids as antibacterial agents via the antisense principle*, Exp. Opin. Invest. Drugs, 10:337-339, 2001.

Ohshima, A., et al., *In-Vivo duplication of genetic elements by the formation of stem-loop DNA without an RNA intermediate*, PNAS, 89(3): 1016-1020, 1992.

Pierce, M.L., et al., *Construction of a directed hammerhead ribozyme library: towards the identification of optimal target sites for antisense-mediated gene inhibition*, Nucleic Acids Research, 26(22): 5093-5101, 1998.

Rapaport, et al., *Antimycobacterial activities of antisense oligodexoynucleotide phosphorthioates in drug resistant strains*, PNAS, 93:709, 1996.

Roth, A. and Breaker, R., *An amino acid as a cofactor for a catalytic polynucleotide*, Proc. Natl. Acad. Sci., 95:6027-6031, 1998.

Schlaak, et al., *Antisense phosphorthioate oligonucleotides to the p65 subunit of NF-kappaB abrogate fuliminant septic shock induced by S. typhimurium in mice*, Scand. J. Immunol., 54:399-400, 2001.

Schleef, M., et al., *Plasmid DNA for pharmaceutical applications*, Dev. Biol. (Basel), 104: 25-31, 2000.

Seidman, et al., *Introduction of plasmid DNA into cells IN*, Current Protocols in Molecular Biology, Unit 1.8, 1997.

Sun, Lun-Quan, et al., *Suppression of Smooth Muscle Cell Proliferation by a c-myc RNA-cleaving Deoxyribozyme*, Journal of Biological Chemistry, 274 (24): 17236-17241, 1999.

Takeuchi, O., et al., *Differential Roles of TLR2 and TLR4 in Recognition of Gram-Negative and Gram-Positive Bacterial Cell Wall Components*, Immunity, 11: 443-451, 1999.

Uhlman, E., *Oligonucleotide Technologies: Synthesis, Production, Regulations and Application*, Expert Opinion on Biological Therapy, 1: 319-328, 2001.

Ulevitch, R., et al., *Recognition of Gram-negative bacteria and endotoxin by the innate immune system*, Current Opinion in Immunology, 11:19-22, 1999.

Vincent, et al., *Clinical Trials of Immunomodulatory Therapies in Severe Sepsis and Septic Shock*, Clinical Infectious Diseases, 34:1084-1093, 2002.

Wheeler, A., et al., *Treating Patients with Severe Sepsis*, New England Journal of Medicine, 340(3): 207-214, 1999.

\* cited by examiner

FIG. 1

Stem-loop structure formed by single-stranded DNA

TREATMENT OF HSV-RELATED PATHOLOGIES USING SSDNA

This application is a continuation-in-part of application Ser. No. 10/136,218, entitled IN VIVO ssDNA EXPRESSION VECTORS FOR ALTERING GENE EXPRESSION, filed May 1, 2002 now abandoned, and application Ser. No. 09/397,782, entitled IN VIVO PRODUCTION OF ssDNA USING REVERSE TRANSCRIPTASE WITH PREDEFINED REACTION TERMINATION VIA STEM-LOOP FORMATION, filed Sep. 16, 1999 now abandoned.

The present invention relates to the treatment of HSV-related pathologies using a composition that produces ssDNA in vivo for altering the expression of genes involved in HSV replication. More particularly, the present invention relates to a composition and method for delivering the information required for production of ssDNA in vivo for altering the function of a gene or genes involved in replication and self-protection of HSV against the host immune system by topical application to an affected site.

Herpes simplex virus types I and II (HSV-I and HSV-II) are the etiological agents of several clinically significant pathologies including oropharyngeal infections, skin infections, ocular infection, and central nervous system disorders such as meningitis and encephalitis (see, for instance, U.S. Pat. No. 5,795,721). HSV seropositive individuals are found in virtually all human populations. It is estimated that more than 60% of the population is seropositive for HSV-I and more than 16% of the population is seropositive for HSV-II.

Primary HSV is often asymptomatic. Whether asymptomatic or not, HSV infection invariably leads to establishment of latent viral infection in nerve cells. No known treatment is available for latent infection and the persistent and frequent outbreaks it provokes. The consequences of latent infection cover a spectrum from no symptoms to repeated and/or severe episodes of the active form of the disease.

As used herein, the term "HSV" is intended to refer to all of the known and yet to be discovered and/or identified strains of herpes simplex virus, including of the known and yet to be discovered and/or identified strains of herpes simplex and/or other viruses, as well as human papilloma (HPV) and varicella zoster (VZ) viruses, that share some of the same genes and/or modes of infection and replication, and the term "HSV-related pathology" is intended to refer to any pathological condition in which HSV or these other related viruses are a causative agent and/or in which such viruses have been and/or will be implicated, even if HSV or these other viruses are not the cause of the pathology (for instance, if HSV infection is a symptom and/or consequence of the pathological condition). Of the more than 100 known human papilloma virus types (HPVs), certain "high risk" HPVs are known that are associated with cervical carcinoma and a pathologically distinct group of oropharyngeal tumors. Other HPVs are associated with cutaneous tumors, particularly epidermodysplasia verruciformis and non-melanoma skin cancers. An HPV-associated tumor can arise from a single accidental integration event of the viral genome into a host cell chromosome and is a terminal event for the viral life cycle. Even though integration does not occur at specific chromsomal hot spots in the human genome, it follows a consistent pattern with respect to the viral genome and expression of the HPV E6 and E7 genes is consistently retained. The normal function of E6 and E7 is to establish and maintain a cellular milieu that allows for viral genome replication. E6 and E7 target important cellular regulatory growth circuits, for instance, the p53 and retinoblastoma tumor suppressors, respectively. Uncontrolled expression of the E6 and E7 proteins as a consequence of viral integration is paramount to the establishment and maintenance of the tumorigenic state. In addition, expression of E6 and E7 increases genomic instability of the host cell, thus accelerating malignant progression.

Fortunately, most HSV-related pathologies are not life-threatening, although they do represent a significant proportion of doctor visits for sexually transmitted diseases. Affected individuals often seek ameliorative treatment to counteract the discomfort caused by HSV induced lesions. The more serious and potentially life-threatening HSV-related CNS pathologies occur infrequently in adult and children. Among neonates, the HSV infection is almost always symptomatic, and over 50% are afflicted by CNS disorders. Without appropriate treatment, CNS infection in neonates leads to greater than 60% mortality. Even with treatment, there is significant mortality in affected neonates. Estimates of neonatal herpes infection are approximately 1 in 4000 live births. Two-thirds of neonatal herpes is attributable to HSV-II. Due to the increasing percentage of HSV-II infected women (20% in the U.S.), neonatal herpes presents a senous public health problem and, so far as is known, there is no effective treatment for this pathology.

There is, therefore, a long-felt and unfulfilled need for effective treatment against these, and other HSV-related pathologies. Known treatments simply are not addressing this need, and it is a primary object of the present invention to provide an effective treatment against HSV-related pathologies for topical application to an affected site, and specifically, to provide a treatment that alters the expression of the genes implicated in the replication and self-protection of HSV against the host immune system.

The HSV genome is a double-stranded, closed, circular DNA molecule consisting of $1.5 \times 10^5$ base pairs, encoding more than 75 polypeptides (Roizman, B., and Sears, A. E., Herpes simplex viruses and their replication, in B. N. Fields and D. M. Knipe (ed.), Fundamental Virology, 2nd Ed., pp. 849-895, Raven Press, 1991). The infective HSV life cycle is governed by three stages of gene expression, referred to as immediate-early (IE), middle and late (also referred to as $\alpha$, $\beta$, and $\gamma$). Each of these stages results in expression of genes whose products are required for subsequent event in the HSV life cycle, culminating in production and release of infective HSV virions.

Following entry of the HSV virion into the cell, its protein coat is shed, releasing a capsid structure that transports the viral genome to the nuclear pores and into the nucleus. Entry into the nucleus marks the beginning of the immediate-early stage. Five IE genes, $\alpha 4$—ICP4, $\alpha 0$—ICP0, $\alpha 27$—ICP27/UL 54, $\alpha 22$—ICP22/US1, and $\alpha 47$—ICP47/US12, are expressed and function in the earliest stages of the productive infection cycle. This immediate-early stage of infection is termed the "$\alpha$" phase of gene expression, and is mediated by the action of $\alpha$-TIF through its interaction with cellular transcription factors at specific enhancer elements associated with the individual $\alpha$-transcript promoters. At least three of the protein products of these genes, ICP0, ICP4, and ICP27, are factors involved in regulation of HSV gene expression (ICP, infected-cell polypeptide). These regulatory factors are expressed throughout the viral life cycle, and serve to control the complex patterns of gene activation, repression, and de-repression that determine the course of HSV proliferation. Middle ($\beta$) genes primarily encode proteins involved in DNA replication and late ($\gamma$) genes encode structural proteins involved in packaging and assembling mature virions.

The ICP4 protein is the major transcriptional regulator of HSV gene expression. (Roizman and Sears, supra). The ICP4 gene (also known as the $\alpha 4$ gene) encodes a polypeptide of 1298 amino acids with a predicted molecular weight of 133,000 daltons. The mature ICP4 protein exists as a homodimer of 350,000 daltons; the large molecular weight reflects post-translational modifications. The ICP4 homodimer is a double-stranded DNA binding protein which functions both as a transcriptional repressor and activator of HSV gene expression (Beard, P., S. Faber, K. Wilcox, and L. Pizer, Herpes simplex virus immediate-early infected-cell polypeptide 4 binds to DNA and promotes transcription, Proc. Natl. Acad. Sci. USA. 83:4016-4020 (1986); Everett, R. D., Promoter sequence and cell type can dramatically affect the efficiency of transcriptional activation induced by herpes simplex virus type 1 and its immediate-early gene products Vmw175 and Vmw 110. J. Mol. Biol. 203:739-752 (1988); Everett, R. D., J. Didonato, M. Elliott, and M. Muller, Herpes simplex virus type 1 polypeptide ICP4 bends DNA, 20:1229-1233 (1992); Faber, S., and K. Wilcox, Association of herpes simplex virus regulatory protein ICP4 with sequences spanning the ICP4 gene transcription initiation site. Nucleic Acids Res. 16 (1988); Gu, B., and N. A. DeLuca, Requirements for activation of the herpes simplex virus glycoprotein C promoter in vitro by the viral regulatory protein ICP4, J. Virol. 68:7953-7965 (1994); Gu, B., R. Rivera-Gonzalez, C. Smith, and N. DeLuca, Herpes simplex virus infected cell polypeptide 4 preferentially represses Sp 1-activated over basal transcription from its own promoter, Proc Natl Acad Sci USA. 90:9528-32 (1993); Imbalzano, A., A. Shepard, and N. DeLuca, Functional relevance of specific interactions between herpes simplex virus type 1 ICP4 and sequences from the promoter-regulatory domain of the viral thymidine kinase gene, J. Virol. 64:2620-2631 (1990), Kuddus, R., B. Gu, and N. A. DeLuca, Relationship between TATA-binding protein and herpes simplex virus type 1 ICP4 DNA-binding sites in complex formation and repression of transcription. J. Virol. 69:5568-5575 (1995); Pizer, L., D. Tedder, J. Betz, and K. Wilcox, Regulation of transcription in vitro from herpes simplex virus genes. J. Virol. 60:950-959 (1996); Pizer, L. I., R. D. Everett, D. G. Tedder, M. Elliott, and B. Litman; Nucleotides within both proximal and distal parts of the consensus sequence are important for specific DNA recognition by the herpes simplex virus regulatory protein ICP4, Nucleic Acids Res. 19:477-484 (1991); Poddevin, B., S. Meguenni, I. Elias, M. Vasseur, and M. Blumenfeld, Improved anti-herpes simplex virus type 1 activity of a phosphodiester antisense oligonucleotide containing a 3'-terminal hairpin-like structure, Antisense Res. Dev. 4:147-154 (1994)).

The actual mechanisms by which ICP4 affects transcription are not well understood. The most well-characterized DNA binding sites are those where ICP4 acts as a repressor. Computer analysis of known ICP4 repression sites has led to a definition of a loose consensus binding site: RTCGTCN-NYNYSG (SEQ ID NO:1), where R=A or G, N=any base, Y=C or T, and S=C or G (Disney, G. H., T. A. Mckee, C. M. Preston, and R. D. Everett, The product of varicella-zoster virus gene 62 autoregulates its own promoter, J. Gen. Virol. 71:2999-3004 (1990)).

ICP4 is an essential gene product whose function is required for HSV proliferation. HSV-1 mutants which lack both copies of the ICP4 gene (there are two in different loci in the genome) fail to replicate DNA and produce new virions (DeLuca, N. A., A. M. McCarthy, and P. A. Schaffer, Isolation and characterization of deletion mutants of herpes simplex virus type 1 in the gene encoding immediate-early regulatory protein ICP4. J. Virol. 56:558-570 (1995)). In addition to ICP4, other essential proteins are glycoproteins B and D (gB and gD), ICP27, and several proteins involved in DNA replication (Matthews, J. T., B. J. Terry, and A. K. Field, The structure and function of the HSV DNA replication proteins: defining novel antiviral targets. Antiviral Res. 20:89-114 (1993); Olivo, P. D., N. L. Nelson, and M. D. Challberg, Herpes simplex virus type 1 gene products required for DNA replication: identification and overexpression. J. Virol. 63:196-204 (1989); Roizman, B., and A. E. Sears, supra. As mentioned above, the action of ICP4 is required throughout the HSV life cycle because of its essential role in viral gene expression.

The biochemical and molecular genetic literature on ICP4 has mostly focused on HSV-1. In general, HSV-1 molecular biology has received much more attention than that of HSV-2, but it is generally agreed that the two viruses perform most critical functions in the same manner, with very closely related proteins. Not surprisingly, the ICP4 proteins from HSV-1 and HSV-2 are functionally interchangeable, based on genetic recombination experiments between the two viruses (Smith, C. A., and P. A. Schaffer, Intertypic recombinants of herpes simplex virus types 1 and 2 infected cell polypeptide 4. Virology. 160:176-182 (1987)). These experiments demonstrated that virtually any region of the two genes can be interchanged with no alteration in function. Consistent with these data is the fact that HSV-1 and -2 have nearly identical ICP4 amino acid sequences based on analysis of their respective gene sequences. (McGeoch, D. J., and S. Cook, Molecular phylogeny of the alphaherpesvirinae subfamily and a proposed evolutionary timescale. J. Mol. Biol. 238:9-22 (1994)).

ICP47 is a cytosolic protein that appears to interfere with the transport from cytosol into the ER of peptides designated for presentation by class I MHC mediated by TAP heterodimer. Studies have shown that ICP47 blocks TAP transportation and that ICP47 interacts directly with the TAP-class I complex. The action of ICP47 enables the HSV viruses to "cloak" themselves and elude the host's immune system by producing surface peptides similar to the host's peptides, so that the host does not recognize them as foreign and destroy them. Other viruses seem to produce substances that block part of the host's immune reaction (Hill, A. et al., Nature, 375(6530): 41, 1-5 (1995)).

The composition of the present invention includes a plasmid or other expression vector in a suitable delivery vehicle that includes the information for delivery and subsequent expression in vivo of (a) one or more sequences of interest (SOI) that code for production of a ssDNA sequence in vivo that targets either a target sequence involved in HSV replication, a transcriptional product of such a target sequence, or a translational product of such a target sequence, and (b) the signaling instructions and enzymatic function(s) for producing that ssDNA sequence in vivo. Delivery is accomplished by incorporating the SOI, and the signaling instructions and enzymatic functions, into a viral vector such as an adenoviral vector, a non-viral vector such as a liposome, or a plasmid and delivering that vector in a crème, ointment, lotion, gel, aerosol spray, or similar substance for use as a vehicle for topical application to an affected site. Regardless of whether the information is delivered and/or expressed by a viral vector, by a plasmid and delivery vehicle, or by other mechanism, the phrase "expression vector" is utilized for the purpose of referring to the system for delivering and expressing the information that causes a change in gene function in the host cell.

More specifically, the composition of the present invention includes an expression vector that comprises a cassette into which a nucleic acid sequence is incorporated for use as a template for production of that sequence in a host cell, and subsequent expression within an HSV-infected cell, as a single-stranded DNA (ssDNA) sequence without (or with minimal) flanking sequences that binds to or otherwise interacts with a target gene or its expression components to alter expression of the target gene. The ssDNA that is produced in the infected cell is designed to be complimentary to and/or to otherwise bind to a nucleic acid sequence target comprising a portion of a target sequence involved in the replication of HSV, thereby interfering with, or altering, expression of the desired gene, and for that reason, is sometimes referred to herein as an oligonucleotide, or ODN. As used in this specification, the term "ODN" is intended to refer to: 1) DNA-based oligonucleotides such as triplex-forming oligonucleotides (TFO), antisense ODNs, DNA enzymes and aptamers and 2) RNA-based oligonucleotides such as ribozymes and antisense RNA. All of these molecules modulate gene expression by interacting with DNA, mRNA, or proteins in sequence-specific manner. Also, the term "affected site" is intended to refer to any site at which an HSV infection manifests itself that can be treated by topical application of the composition of the present invention, regardless of whether the site of the infection is, for instance, on the skin, in a body cavity or an opening of the body, or even internal, and regardless of the nature of the tissue that is infected.

One type of therapy that would seem to present an ideal approach to treatment of HSV-related pathologies is antisense therapy. Antisense gene therapy has been successfully used in a variety of applications to down regulate gene function (Jain, K. K., Handbook of Gene Therapy, New York: Hofgrefe & Huber Publishing (1998)). The conventional method for delivery involves synthesizing chemically-modified, specifically sequenced, ODNs in the laboratory and delivering the ODNs in high concentrations systemically. However, conventional antisense therapy is characterized by a number of disadvantages and limitations that have decreased the utility of this type of therapy such that, so far as is known, no effective antisense treatment is available for HSV-related pathologies. The disadvantages and limitations of conventionally delivered antisense therapy include, among other things, the short half-life of the antisense molecule in vivo, non-specific effects, uncertainties as to the mode of action of the antisense sequence, and potential toxic effects as observed in animal studies. For instance, antisense oligonucleotides (ODNs) and their analogs administered intravenously involve problems in cell uptake and distribution (Cossum, P. A., et al., Disposition of the $^{14}$C-labeled phosphorothioate oligonucleotide ISIS 2105 after intravenous administration to rats, 267 J. Pharmacol. Exp. Ther. 1181-1190 (1993), Sands, H., et al., Biodistribution and metabolism of internally $^{13}$H-labeled oligonucleotides. II. 3', 5'-blocked oligonucleotides, 47 Mol. Pharmacol. 636-646 (1995)) as well as toxicity problems due to high blood concentrations (Henry, S. P., et al., Evaluation of the toxicity of ISIS 2302, a phosphorothioate oligonucleotide, in a 4-week study in CD-1 mice, 7 Antisense Nucleic Acid Drug Dev. 473-481 (1997), Henry, S. P., et al., Comparison of the toxicity profiles of ISIS 1082 and ISIS 2105, phosphorothioate oligonucleotides, following subacute intradermal administration in Sprague-Dawley rats, 116 Toxicology 77-88 (1997)).

The major difference between conventional antisense or other ODN mediated therapy and the instant invention is that the ssDNA of the instant invention is produced as a phosphodiester sequence inside the cell. This approach to production of antisense ODNs eliminates the need to use ODN analogs such as phosphorothioates and the numerous problems attendant with injecting large concentrations of said analogs into the blood stream.

The antisense ODN analogs used most in antisense therapies are phosphorothioates or methylphosphonates. However, phosphorothioate ODNs tend to bind serum and intracellular proteins nonspecifically (Crooke, S. T., et al., Pharmacokinetic properties of several novel oligonucleotide analogs in mice, 227 J. Pharmacol. Exp. Ther. 923-937 (1996), Gao, W. Y., et al., Phosphorothioate oligonucleotides are inhibitors of human DNA polymerases and RNase H: implications for antisense technology, 41 Mol. Pharmacol. 223-229 (1992)), and at higher concentrations, inhibit RNase H activity (Crooke, S. T., et al., Kinetic characteristics of *Escherichia coli* Rnase H: Cleavage of various antisense oligonucleotide-RNA duplexes, 312 Biochem. J. 599-608 (1995)). Phosphorothioate ODNs have a lower Tm (an average of 0.5° C. per base pair) for RNA than does natural DNA (Crooke, S. T. and B. LeBleu, Antisense research and application, Boca Raton: CRC Press (1993)). This lower Tm requires that phosphorothioate ODNs typically be longer than phosphodiester DNA oligonucleotides for effective binding. However, an increase in the length of the ODN can cause a loss of hybridization specificity (Toulme, J. J., et al., Antisense technology: A practical approach, in C. Lichtenstein and W. Nellen (Eds.), New York: IRL Press, pp. 39-74 (1997)). In addition, methylphosphonate ODNs do not activate RNase H enzyme activity (Maher, L. J, et al., Inhibition of DNA binding proteins by oligonucleotide-directed triple helix formation, 245 Science 725-730 (1989), Miller, P. S., Oligodeoxynucleotides: Antisense inhibitors of gene expression, in J. S. Cohen (Ed.), Boca Raton: CRC Press, p. 79 (1989)) and are eliminated rapidly (Chen, T. L., et al., Disposition and metabolism of oligodeoxynucleoside methylphosphonate following a single i.v. injection in mice, 18 Drug Metab. Dispos. 815-818 (1990)). For a summary of many different strategies that have been attempted for the delivery of ODNs, and their varying degrees of success, see Akhar, S., et al., The delivery of antisense therapeutics, 44 Adv. Drug Delivery Rev. 3-21 (2000).

Another approach to the use of ODNs for treatment of HSV-related pathologies that might be used to target the genes involved in HSV replication is to administer molecules that have catalytic activity against a target gene and/or the transcriptional product of the target gene. For instance, ribozymes are capable of catalyzing the cleavage of specific mRNA sequences, and are thought to be potentially more efficient in targeting the target gene than antisense ODNs because of their catalytic capability. Woolf, T. M., To cleave or not to cleave: Ribozymes and antisense, 5 Antisense Res. Dev. 227-232 (1995). Ribozymes have been used as inhibitors of gene expression and viral replication. Jain, supra (1998). Unlike antisense ODNs, ribozymes can be delivered either endogenously, such as by using viral vectors, or exogenously. However, ribozymes have limited stability due to degradation by RNases in vivo. Jain, supra (1998).

Using in vitro selections, several small single-stranded DNAs have recently been demonstrated to catalyze the cleavage of RNA (Breaker, R. R., Catalytic DNA: In training and seeking employment, 17 Nature Biotechnology 422-423 (1999)), thereby offering the promise of targeted activity against specific genes. The patent and scientific literature describes a number of these short deoxynucleic acid sequences that have been shown to have catalytic activity (see, Breaker, R. R. and G. F. Joyce, 1 Chem. Biol. 223-229 (1994); Cuenoud, B. and J. W. Szostak, 375 Nature 611-613 (1995); Santoro, S. W. and G. F. Joyce, 94 Proc. Natl. Acad. Sci. USA 4262-4266 (1997); Faulhammer and M. Famulok, 269 J. Molec. Bio. 188-203 (1997); Carmi, N, et al., 95 Proc. Natl. Acad. Sci. USA (1998); Li, Y. and R. R. Breaker, 96 Proc. Natl. Acad. Sci. USA 2746-2751 (1999) and U.S. Pat. Nos. 5,807,718 and 5,910,408), including the so-called "10-23 DNA enzyme" and other ssDNA sequences that act, for instance, as copper-dependent DNA ligases and calcium-dependent DNA kinases. The catalytic efficiency of such sequences has been demonstrated for cleaving mRNA targets at $10^{-9}$ mol/min in the presence of divalent magnesium, thereby offering the opportunity for targeted destruction of substrate molecules (see, for instance, R. R. Breaker, supra (1999)). Although the art appears to recognize the potential for use of this enzymatic activity for therapeutic purposes, so far as is known, no system is available for producing target-specific enzymatic nucleic acid sequences for treatment of HSV-related pathologies. Consequently, another object of the present invention is to provide a treatment for HSV-related pathologies that involves the delivery of a DNA expression vector to an affected site that includes a cassette that directs the synthesis of ssDNA containing a sequence that specifically cleaves specified mRNA target(s) produced from one or more genes involved in the replication of HSV in that target cell to alter the expression of the gene producing that target mRNA(s).

Because secondary structure folding may be critical to the catalytic function of the enzymatic sequence of the ssDNA, it is another object of the present invention to provide a composition for treatment of HSV-related pathologies comprising an expression vector for producing ssDNA including a DNA enzyme sequence without undesirable intervening or flanking nucleotide bases so as to preserve the enzymatic function of the ssDNA against a target nucleic acid, for use in altering expression of a gene involved in replication of HSV including that target nucleic acid.

It is therefore another object of the present invention to provide a method for treating HSV-related pathologies comprising administering an expression vector for producing ssDNA of any nucleotide sequence intracellularly in vivo that functions as (but is not limited to) an inhibitory nucleic acid for, for instance, targeting one or more target sequences in anti-sense or DNA enzymatic fashion, to down regulate a gene product or a viral gene involved in HSV replication, for instance, by binding to proteins that recognize a nucleic acid sequence.

Another object of the present invention is to provide a composition for treatment of HSV-related pathologies that comprises an expression vector for producing ssDNA of any nucleotide sequence in vivo that functions as (but is not limited to) an excitatory nucleic acid for, for instance, binding to one or more target chromosomal sequences to increase production of a gene or to "switch on" a target gene for inhibiting replication of HSV in vehicle for topical application to an affected site.

Another object of the present invention is to provide a composition for treatment of HSV-related pathologies that comprises an expression vector for producing ssDNA in vivo that is designed to favor binding to duplex, either endogenous (native DNA) or the double-stranded DNA comprising the viral genome, to form triplex structures that interfere with normal gene transcription and regulation of a target gene involved in the replication of HSV in a vehicle for topical application to an affected site.

Another object of the present invention is to produce ssDNA within one or more target cell populations for the purpose of disrupting and/or altering one or more of the cell functions required for HSV replication.

Yet another object of the present invention is to provide a composition and method in which an expression vector for producing ssDNA into which secondary structures are designed so that the ODN(s) produced by the vector in one or more target cell populations bind to and/or otherwise inhibit or activate various cellular functions in HSV proliferation that rely on the catalytic action of a protein or on nucleic acid protein interaction such as transcription, translation, and DNA proliferation replication.

Another object of the present invention is to provide a composition for treatment of HSV-related pathologies that comprises an expression vector for in vivo production of ssDNA including a sequence exhibiting catalytic activity against mRNA targets of the gene(s) involved in viral replication for transfection into HSV-infected cells that overcomes the obstacles to delivery of direct administration of ssDNA by lipofection, direct cellular uptake, and/or microinjection when delivered in an appropriate vehicle for topical application to an affected site.

Another object of the present invention is to provide a composition for treatment of HSV-related pathologies that comprises an expression system for in vivo production of ssDNA including a sequence exhibiting catalytic activity against mRNA targets produced by a specific gene or genes involved in viral proliferation or other viral functions for transfection into HSV-infected cells that overcomes the obstacles to delivery of direct administration of ssDNA by lipofection, direct cellular uptake, and/or microinjection when suspended in a medium for topical application to an affected site.

Another object of the present invention is to provide a composition for treatment of HSV-related pathologies that comprises an expression system for in vivo production of ssDNA including a sequence exhibiting catalytic activity against mRNA targets produced by a specific gene or genes involved in viral proliferation or other viral functions for transfection into HSV-infected cells that overcomes the obstacles to delivery of direct administration of ssDNA by lipofection, direct cellular uptake, and/or microinjection for topical application to an affected site.

Another object of the present invention is to provide a composition for treatment of HSV-related pathologies that comprises an expression vector for in vivo production of ssDNA including a sequence exhibiting catalytic activity against mRNA targets of the gene(s) involved in viral replication for transfection into HSV-infected cells in a vehicle that can be applied topically to HSV infected cells.

Another object of the present invention is to provide pharmacologically acceptable compositions for delivering an inhibitory or excitatory nucleic acid sequence, including a sequence with enzymatic activity, to HSV-infected cells in a manner that produces a therapeutic effect.

This listing of the objects of the present invention is not intended to be a list of all the objects of this invention. There are a number of other cellular functions that are used to advantage by replicating and/or latent HSV virus that are mediated by the cellular genome which can be altered in accordance with the teachings of the present invention and which are amenable to regulation by in vivo production of ssDNA. In the interest of brevity and practicality, those many other functions are not mentioned here. Instead, this list of some of the objects of the present invention is provided for exemplification and is not intended to limit the scope of the invention.

These objects are provided by a composition for treating HSV-related pathologies comprising a vector including the information required for expression of a ssDNA sequence in vivo that targets or otherwise interacts with a nucleic acid target sequence involved in the replication of HSV in a suitable vehicle for topical application to an affected site. In a preferred embodiment, the vector comprising the present composition includes a cassette comprised of a sequence of interest flanked by an inverted tandem repeat, a 3' pruner binding site (PBS), and a gene encoding a reverse transcriptase for transcribing the mRNA transcript of the cassette from the PBS to release a single-stranded cDNA transcript in a cell into which the expression vector has been incorporated at the affected site. The sequence of interest is comprised of a nucleic acid sequence that produces a sequence of nucleic acids that targets, binds to, or otherwise interacts with the target nucleic acid sequence that is involved in proliferation of HSV when reverse transcribed to alter expression of the target sequence.

Also provided is an improved method for treating HSV-related pathologies involving the application of a topical ointment to an affected site wherein the improvement comprises contacting the affected site with a vector including the information required for expression of a ssDNA sequence in vivo that targets a dsDNA sequence that is involved in the proliferation of HSV by inclusion of said vector in the topical ointment.

Several embodiments of the invention are illustrated in the figures, in which.

In this description of the present invention, an expression vector is described for use in producing single-stranded deoxyribonucleic acid (ssDNA) of virtually any predefmed or desired nucleotide base composition intracellularly in vivo in HSV-infected cells, with or without flanking nucleotide sequences, that is either substantially homologous or complementary to the target sequence for binding to the target sequence to alter the expression of that sequence and/or inactivate or destroy the product of that sequence. The expression vector is delivered to the infected cells at an affected site by topical application in a crème, lotion, ointment, spray, or gel.

Figure 1:
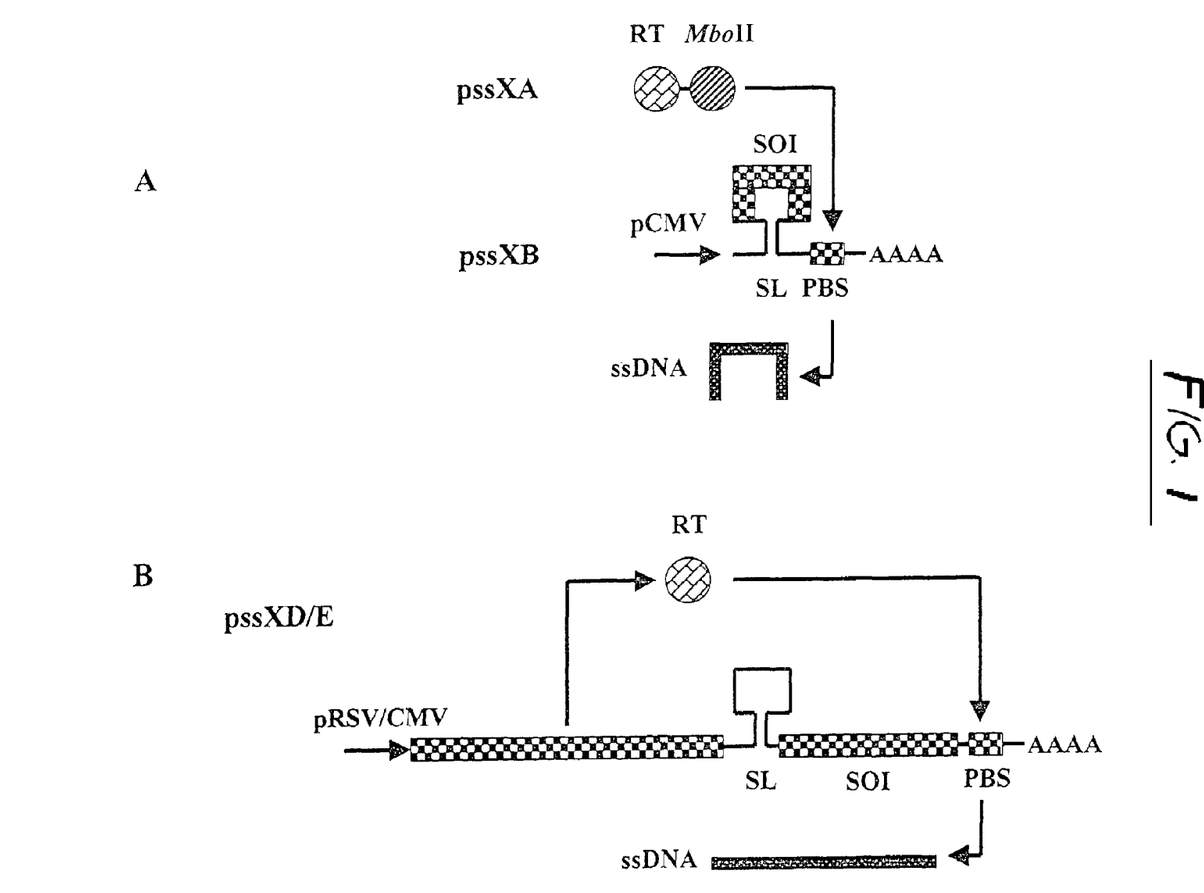
FIG. 1 is a schematic illustration of the production of ssDNA in a host cell in accordance with the teachings of the present invention.

In one embodiment, the expression vector of the present invention (as used herein, the term "vector" refers to one or more plasmids or modified viral or non-viral recombinant biological constructs used to deliver and manipulate synthesized and/or naturally occurring nucleic acid sequences) is designed to produce a sequence of interest as a ssDNA molecule, preferably free of most contiguous vector sequences, within an HSV-infected cell. The vector contains all the necessary enzymatic functions and signaling instructions for producing ssDNA in the infected cell. As shown in FIG. 1 (illustrating the use of a plasmid as an expression vector constructed in accordance with the teachings of the present invention), the infected cell to which the vector is delivered produces an RNA transcript, driven by an eukaryotic promoter, that is used as a template to direct the synthesis of the desired single-stranded DNA sequence for altering the function of a gene involved in replication of HSV.

The ssDNA produced in vivo using the expression vector that is delivered to an affected site in the composition described herein may be any ODN, including ODNs that function as inhibitory nucleic acids or excitatory nucleic acids. Inhibitory nucleic acids may be ssDNA synthesized from the mRNA template, or the mRNA template itself, that can specifically bind to a complementary nucleic acid sequence in the infected cell. By binding to the appropriate target nucleic acid sequence, an RNA-RNA, a DNA-DNA, or RNA-DNA duplex or triplex is formed. More commonly, these nucleic acid sequences are termed "antisense" sequences because they are usually complementary to the sense or coding strand of the gene, but the "sense" sequence is also utilized in the cell for therapeutic purposes. The term "inhibitory nucleic acids" as used herein, therefore, includes both "sense" and "antisense" nucleic acids, but as set out below, is not limited to sense and/or antisense nucleic acids.

By binding to a target sequence (and by the phrase "target sequence," it is intended to refer not only to the target sequence itself, regardless of whether the target sequence is a sequence that is endogenous to the host cell and/or a part of the genome of the virus, but also to the transcriptional and translational products of that target sequence), an inhibitory nucleic acid alters the function of a gene involved in viral replication. This alteration (usually an inhibitory effect) results from, for example, blocking DNA transcription, processing or poly(A) addition to mRNA, DNA replication, translation, or promoting inhibitory mechanisms of the cells (such as promoting RNA degradation). Inhibitory nucleic acid methods therefore encompass a number of different approaches, functioning in several different ways, for altering gene expression in an HSV-infected cell. Because of the many ways in which they function to alter gene function, broad reference is made herein to binding, or otherwise interacting with, the target sequence. The different types of inhibitory nucleic acid technologies are described in Helene, C. and J. Toulme (1049 Biochim. Biophys. Acta. 99-125 (1990)), hereinafter referred to as "Helene and Toulme," which is incorporated herein in its entirety by this specific reference thereto.

In brief, inhibitory nucleic acid therapy approaches can be classified into (1) those that target DNA sequences, (2) those that target RNA sequences (including pre-mRNA and mRNA), (3) those that target proteins (sense strand approaches), and (4) those that cause cleavage or chemical modification of the target nucleic acids such as the ssDNA enzymes, including the so-called "10-23 enzyme" as described herein. The first approach contemplates several categories. Nucleic acids are designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. More commonly, inhibitory nucleic acids are designed to bind to mRNA or mRNA precursors. Inhibitory nucleic acids are also used to prevent maturation of pre-mRNA. Inhibitory nucleic acids may also be designed to interfere with RNA processing, splicing or translation. In the second approach, the inhibitory nucleic acids are targeted to mRNA. In this approach, the inhibitory nucleic acids are designed to specifically block translation of the encoded protein. Using this second approach, the inhibitory nucleic acid is used to selectively suppress certain cellular functions by inhibition of translation of mRNA encoding critical proteins. An example of such an inhibitory nucleic acid is the sequence that is complementary to regions of c-myc mRNA, which inhibits c-myc protein expression in a human promyelocytic leukemia cell line, HL60, which overexpresses the c-myc proto-oncogene (Wickstrom E. L., et al., 85 Proc. Natl. Acad. Sci. USA 1028-1032 (1988) and Harel-Bellan, A., et al., 168 Exp. Med. 2309-2318 (1988)). As described in Helene and Toulme, inhibitory nucleic acids targeting mRNA have been shown to work by several different mechanisms to inhibit translation of the encoded protein(s).

Inhibitory nucleic acids can also utilize the third approach of designing the "sense" strand of the gene or mRNA to trap or compete for enzymes or binding proteins involved in mRNA translation as described in Helene and Toulme. Lastly, inhibitory nucleic acids are used to induce chemical inactivation or cleavage of the target genes or mRNA. Chemical inactivation can occur by several mechanisms. In a particularly preferred embodiment, the expression vector of the present invention includes a sequence of interest that, when transcribed inside the host cell, functions as an enzyme to effect the cleavage of the target nucleic acid.

Figure 2:
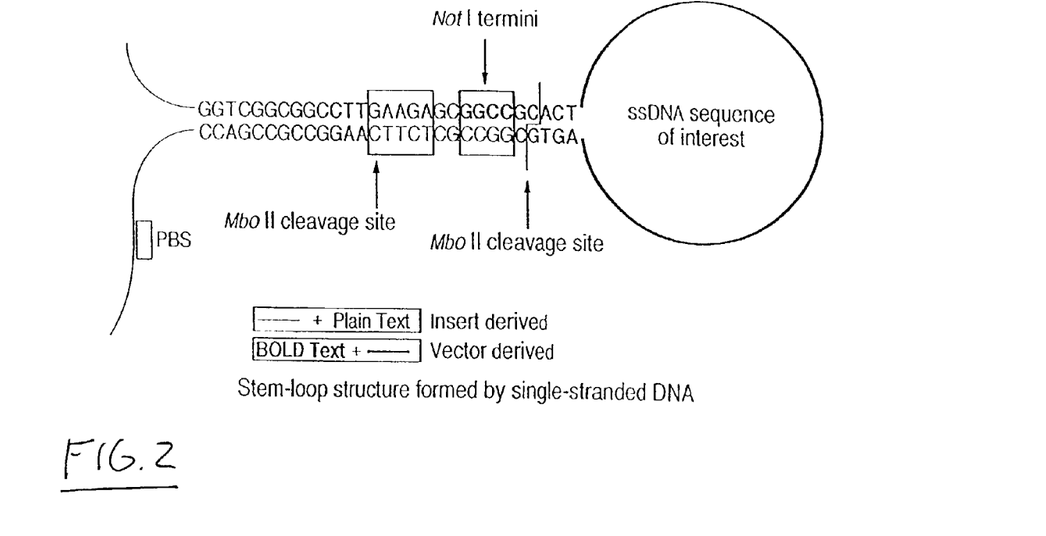
FIG. 2 is a schematic illustration of the stem-loop intermediate formed by the method illustrated in FIG. 1. The stem of the stem-loop structure shown comprises an Mbo II cleavage site. The 5' leg of the stem structure shown comprises the sequence, GGTCGGCGGC CTTGAAGAGC GGCCG-CACT[SEQ ID NO: 10].

Focusing further on the expression vector comprising the composition of the present invention, the vector comprises a set of genetic elements adapted for delivery into a cell to produce ssDNA in vitro or in vivo for altering expression of a target sequence involved in HSV proliferation that includes (A) an RNA dependent DNA polymerase (reverse transcriptase) gene, and
(B) a cassette including (1) an inverted tandem repeat (IR), (2) one or more sequences of interest (SOIs) located (a) between the inverted repeat (IR), (b) 3' to the IR, or (c) both between the IR and 3' to the IR and (3) a primer binding site (PBS) for the reverse transcriptase that is located 3' to the IR as shown in FIG. 2.

Although not required, the expression vector also preferably includes the functions and signaling instructions for transcription of these components in vivo and the functions and signaling instructions for translation of the reverse transcriptase (RT) gene. Additional elements that are optionally included in the expression vector comprising the composition of the present invention may include one or more of an RNAse gene, usually associated with the RT gene, a restriction endonuclease (RE) gene (for a purpose described below), a downstream polyadenylation signal sequence for expression in eukaryotic cells so that the mRNA produced by the sequence of interest includes a poly(A) tail (see FIG. 1), and a DNA sequence having enzymatic activity when the linearized ssDNA folds into the appropriate secondary configuration. Although the present invention is not so limited, in one embodiment of the expression vector, the DNA enzymatic sequence is located within a sequence of interest, regardless of whether the sequence of interest is located between the inverted repeat (IR) or between the 3' aspect of the IR and the PBS.

As noted above, in a first embodiment of the composition of the present invention, the expression vector comprises a plasmid including the three above-listed elements of the cassette, namely, a primer binding sequence (PBS) matched to the reverse transcriptase (RT), a sequence of interest (SOI), and an inverted repeat (IR). In this plasmid, exemplified by the plasmid pssXE shown in FIG. 3, the SOI is located either between the inverted tandem repeats or in a 5' position (with respect to the mRNA transcript) to the PBS, the PBS being located at the most 3' aspect of the mRNA transcript, or in both locations. In other words, the SOI is located (1) between the IR, (2) between the IR and the PBS, and/or (3) both between the IR and between the IR and the PBS. The PBS, SOI, and IR reside in the untranslated 3' portion of the RT polyprotein in the E plasmid shown in FIG. 3. When the RT-RNAse H component of the plasmid is transcribed under control of an appropriate promoter (in the embodiments described herein, the CMV promoter was utilized), the resulting mRNA transcript contains the coding region for the RT-RNAse H polyprotein and, at the end of translation at the stop signals, the additional mRNA transcript contains (3' to this translated protein) these three elements with further 3' downstream signaling events for polyadenylation signals, which remain intact from the RT-RNAse H component.

Figure 3:
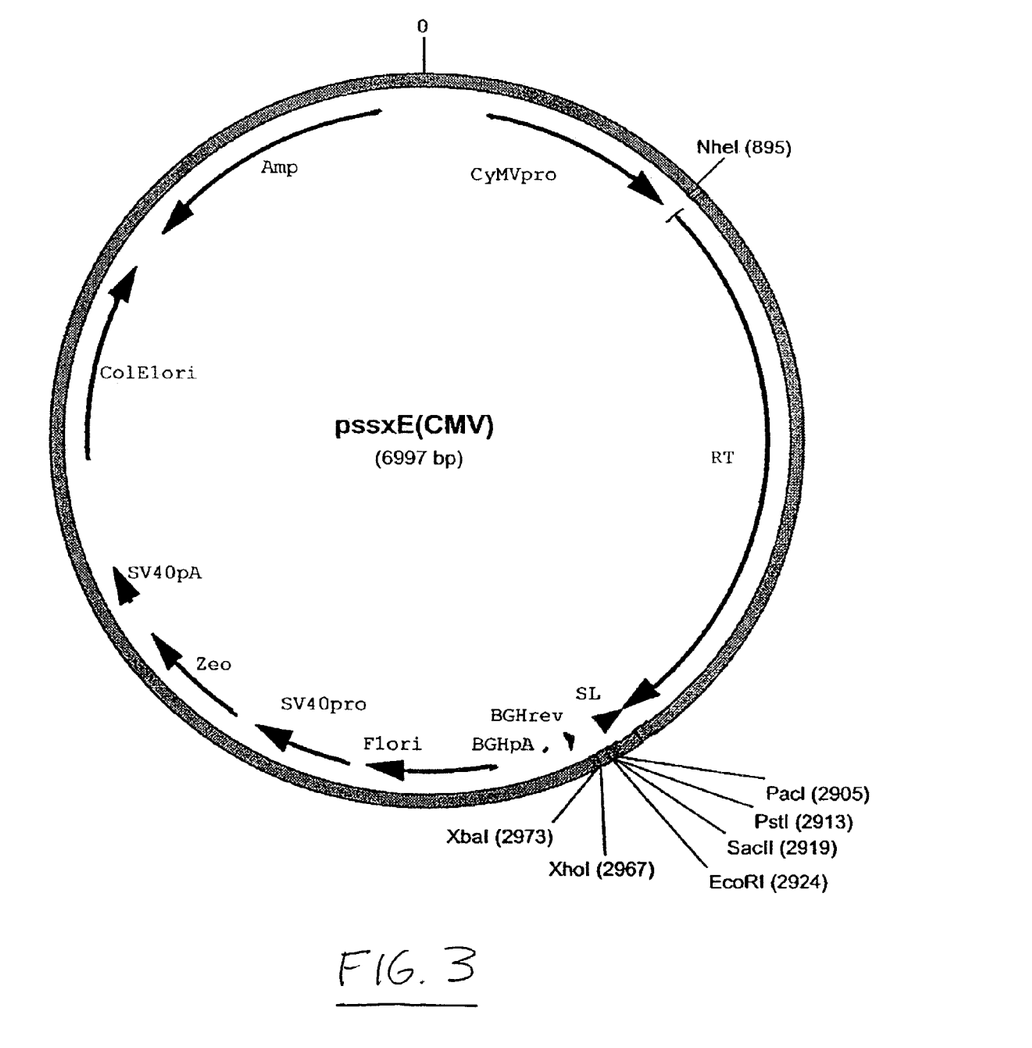
FIG. 3 represents a schematic illustration of the pssXE plasmid comprising a preferred embodiment of an expression vector constructed in accordance with the teachings of the present invention.
Figure 4:
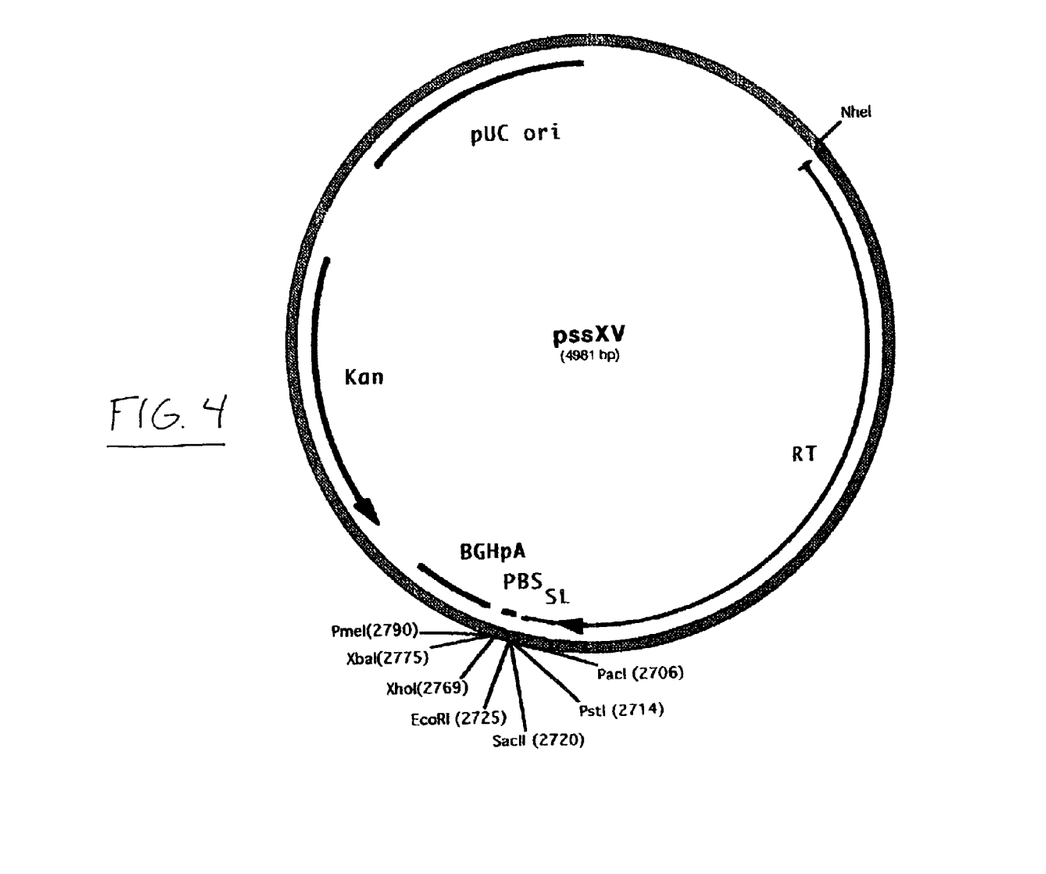
FIG. 4 represents a schematic illustration of the pssXV plasmid comprising a preferred embodiment of an expression vector constructed in accordance with the teachings of the present invention.

The pssXE and pssXV plasmids shown in FIGS. 3 and 4 comprising the composition of the present invention include a multiple subcloning site that facilitates subcloning of the SOI. As known in the art, a multiple cloning site (MCS) containing a number of restriction enzyme (usually 4-10) recognition sequences, is designed to make a vector more flexible for the insertion of different DNA sequences. As will be apparent to those skilled in the art, however, only restriction enzymes that do not cut the vector can be chosen. Although many are known, the following is a list of restriction enzymes that can be selected for use in connection with pssXE, or any other plasmid constructed in accordance with the teachings of the present invention:

AflIII, AscI, BsiWI, BsmBI, BspMI, BsrGI, BsBI, ClaI, E1047III, HpaI, NarI, PF1MI, PshAI, SfiI, SgfI, SrfI, Sse8387I, SwaI, XcmI, as well as the EcoRI, PacI, PstI, and SacII sites that were selected for inclusion in the pssXE vector. Those skilled in the art who have the benefit of this disclosure will recognize that these particular cloning sites were chosen for the particular systems described herein and that other cloning sites may be equally useful for this same purpose.

The nucleic acid sequence that is referred to herein as a cassette provides the template for synthesis of ssDNA in HSV-infected cells. It is this element that includes the SOI, IR, and PBS, and this genetic element is preferably regulated by an appropriate wide spectrum or tissue-specific promoter/enhancer, such as the CMV promoter, or a combination of promoters/enhancers, located upstream of the genetic element. The promoter/enhancer can either be a constitutive or inducible promoter. As set out in more detail below, those skilled in the art who have the benefit of this disclosure will recognize that a number of other eukaryotic promoters may be used to advantage to control expression of the SOI including SV-40, RSV (non-cell type specific) or tissue-specific glial fibrillary acidic protein (GFAP).

Two plasmids of the current invention, having no cloned SOIs, have been appropriately deposited under the terms of the Budapest Treaty with the American Type Culture Collection, located at 10801 University Blvd. in Manassas, Va. 20110-2209, and have the following identifiers: (1) pssXE (PTA-8501, deposited Jun. 12, 2007) has a CMV promoter and an SV40poly-A sequence; and (2) pssXV (PTA-8503, deposited Jun. 12, 2007) also has a CMV promoter and a bovine growth hormone (BGH) poly-A sequence.

The primer binding site (PBS) for initiation of priming for cDNA synthesis is located between the 3' IR and the polyadenylation signal. The PBS is a sequence that is complementary to a transfer RNA (tRNA) which is resident within the eukaryotic target cell. In the case of the mouse Maloney reverse transcriptase (MoMULV RT) that is one RT that may be utilized in conjunction with the present invention, the PBS takes advantage of the proline tRNA. The PBS utilized in connection with the expression vector comprising the presently preferred embodiment of the invention described herein including the RT gene was taken from the nucleotide sequence of HIV. Y. Li, et al., 66 J. Virology 6587-6600 (1992). However, those skilled in the art who have the benefit of this disclosure will recognize that any PBS that is matched to a particular RT is utilized for this purpose. The PBS is exclusively recognized by a primer tRNA that is endogenous to the target cells. Each tRNA has the ability to recognize a unique sequence (i.e., codon) on the mRNA transcript coding for an amino acid, and has the ability to covalently link to a specific amino acid (i.e., the tRNA becomes "charged" when bound to a specific amino acid). However, a primer tRNA, when bound to the mRNA transcript PBS and not covalently linked with an amino acid (i.e., "uncharged"), may be used to initiate ssDNA synthesis by the RT. Thus, each PBS incorporated into the expression vector comprising the composition of the present invention must contain the unique sequence recognized by the primer tRNA, and the primer tRNA must be a primer tRNA that is recognized by the particular RT utilized.

Other retroviral RT/RNAse H genes may be used to advantage in connection with the present invention, it being preferred that the RT/RNase H gene be an RT/RNase H gene that is regulated by an appropriate upstream eukaryotic promoter/enhancer such as the CMV or RSV promoter for expression in human cells. RNA-dependent DNA polymerase/RT genes suitable for use in connection with the present invention include those from retroviruses, such as strains of hepatitis C, lentiviruses such as strains of HIV, bacterial retron elements, and retrons isolated from various yeast and bacterial species. As found in nature, these RNA-dependent DNA polymerases usually have an associated RNase H component enzyme within the same coding transcript. However, the present invention does not require the naturally-occurring RNase H gene for a particular RT. In other words, those skilled in the art will recognize from this disclosure that various combinations of RT and RNase H genes can be spliced together for use in connection with the present invention to fulfill this function and that modifications and/or hybrid versions of these two enzyme systems are available and/or known to those skilled in the art which will function in the intended manner. Those skilled in the art will also recognize that the target cell may itself have sufficient endogenous RNase H to fulfill this function. Similarly, those skilled in the art will recognize that the target cell may itself have sufficient endogenous RT activity from, for instance, prior retroviral infection, to fulfill this function. It will also be recognized by those skilled in the art who have the benefit of this disclosure that the use of a viral vector as the expression vector comprising the composition of the present invention makes possible the use of a number of viral RT genes that are otherwise not well-suited for use in a plasmid expression vector system.

The RT/RNase H gene also preferably includes a downstream polyadenylation signal sequence so that the mRNA produced from the RT/RNase H gene includes a 3' poly(A) tail for mRNA stability. As known to those skilled in the art, multiple poly(A) tails are available and are routinely used for production of expressed eukaryotic genes.

Those skilled in the art will also recognize that a number of tissue-specific or wide spectrum promoters/enhancers, or combinations of promoters/enhancers other than those listed above may also be used to advantage to regulate the RT/RNAse H gene, the RE gene (if utilized), and the sequence of interest. Although a list of all available promoters/enhancers is not needed to exemplify the invention, as noted above, the promoters/enhancers may be constitutive or inducible and may include the CMV or RSV (non-cell type specific) or GFAP (tissue specific) promoters/enhancers listed here and many other viral or mammalian promoters. Representative promoters/enhancers that are appropriate for use in connection with the cassette of the present invention may include, but are not limited to, HSVtk (S. L. McKnight, et al., 217 Science 316 (1982)), human β-globulin promoter (R. Breathnach, et al., 50 Ann. Rev. of Biochem. 349 (1981)), β-actin (T. Kawamoto, et al., 8 Mol. Cell Biol. 267 (1988)), rat growth hormone (P. R. Larsen, et al., 83 Proc. Natl. Acad. Sci. U.S.A. 8283 (1986)), MMTV (A. L. Huang, et al., 27 Cell 245 (1981)), adenovirus 5 E2 (M. J. Imperiale, et al., 4 Mol. Cell. Biol. 875 (1984)), SV40 (P. Angel, et al., 49 Cell 729 (1987)), α-2-macroglobulin (D. Kunz, et al., 17 Nucl. Acids Res. 1121 (1989)), MHC class I gene H-2 kb (M. A. Blanar, et al., 8 EMBO J. 1139 (1989)), and thyroid stimulating hormone (V. K. Chatterjee, et al., 86 Proc. Natl. Acad. Sci. U.S.A. 9114 (1989)). A list of other promoters that may be suitable for use in connection with the cassette of the present inventions includes:

1, SV40 early promoter;
 2. Cytomegalovirus (CMV) promoter;
 3. Elongation factor-1a (EF-1a) promoter;
 4. Thyroxine-binding globulin (TBG) promoter;
 5. Multidrug resistance gene (mdr1) promoter, drug and heat inducible
 6. Heat shock protein (HSP) promoter;
 7. Tet-responsive (TRE) promoter, drug inducible;
 8. HSV (thimine kinase) TK promoter, heat inducible;
 9. Gal4-E1b promoter; drug inducible;
 10. Ubiquitin C(UbC) promoter; and
 11. Telomerase reverse transcriptase (TERT) promoter, tumor-specific.

Those skilled in the art will recognize that this list of promoters is not intended to be all-inclusive and that there are other promoters that will function to advantage when utilized in the espression vector of the present invention.

The RT produced in the cell synthesizes a complementary DNA (cDNA) using as the template the cassette including the SOI described below. The RNase H activity of the RT degrades the mRNA template component of the RNA/cDNA hybrid to produce a ssDNA in vivo.

The gene encoding the RE (if used, and not a required component of the invention) may be any of several genes that encode for REs, and preferably those that are controlled by one or more constitutive or inducible wide spectrum and/or tissue-specific promoters/enhancers such as those listed above. Two REs that have been tested are MboII and FokI, but those skilled in the art who have the benefit of this disclosure will recognize that any RE (type I, II, IIS, or III) site may be included in the IR. These enzymes "clip," or digest, the stem of the stem-loop intermediate described below to linearize the SOI as single-stranded DNA. Expression of the RE gene may be regulated by an appropriate constitutive or inducible promoter/enhancer located upstream from the restriction endonuclease gene such as the CMV or RSV promoter for expression in human cells, in plasmid pssXA. The RE gene also preferably includes a downstream polyadenylation signal sequence so that the mRNA transcript from the RE gene will have a 3' poly(A) tail.

The cassette comprising the expression vector of the composition of the present invention also comprises an inverted tandem repeat (IR). After digestion of the mRNA from the mRNA-cDNA heteroduplex by RNAse H and the release of the ssDNA, the IR causes the ssDNA to fold back upon itself to form the stem of a stem-loop structure, the stem structure being comprised of double stranded, anti-parallel DNA, in the manner described in U.S. Pat. No. 6,054,299 and as shown in FIG. 2, after the cassette is transcribed in the cell and after the RT/RNase H produced by transcription of the genes produces the ssDNA sequence of interest from the mRNA transcript in the cell. One or more RE site(s), which may be cut by the RE produced from the RE gene (in the case of those plasmids that include an RE gene) or by an endogenous RE, may be designed into the double stranded portion, i.e., the IR, that forms the stem of the stem-loop intermediate. The ssDNA that is produced is transcribed with the encoded 5' and 3' regions flanking the stem (made up of the IR) and a loop containing the SOI. The stem is then digested or cleaved by any of the many RE enzymes that recognize the cut site designed into the stem (again, note that the endonuclease recognition site may be designed into the stem even though the RE gene is not included in the vector system of the present invention) to release the ssDNA loop (see FIG. 1). The loop portion of the ssDNA, which does not form any apparent duplex DNA, is immune to RE activity since REs recognize only double stranded DNA as a target substrate.

As noted above, those skilled in the art will recognize that the RE site(s) need not be designed into the IR which forms the stem of the stem-loop intermediate if it is desired to produce ssDNA from an SOI located between the PBS and the IR, with transcription of the cassette terminating at the stem formed by the IR. Another option is to design the IR to contain eukaryotic, prokaryotic, or viral protein DNA binding sites, that act to competitively titer out selected cellular proteins. Combinations of restriction sites or other sequence specific elements may be included in the IR depending on the base pair composition chosen for the IR such that linear or precisely cut stem-loop intermediate forms of ssDNA are produced. It is generally preferred to use synthetically constructed sequence specific elements in the IR since it is unlikely that a naturally occurring inverted repeat would have the properly aligned restriction sites.

As noted above, the cassette that comprises the expression vector of the composition of the present invention may also include a DNA sequence with catalytic activity. Because of the inclusion of the so-called "DNA enzyme" in the cassette (and in the embodiment described herein, the DNA enzyme is located within the sequence of interest), the present invention is used to particular advantage when the sequence of interest serves as the template for synthesis of an inhibitory nucleic acid that is an antisense sequence, a triplex-forming oligonucleotide (TFO), or a DNA enzyme sequence. The nucleic acid sequence having enzymatic activity utilized in the method of altering gene expression described herein is the 10-23 DNA enzyme (Santoro and Joyce, supra (1997)). The enzymatic sequence is inserted into the cassette in either or both of the two locations, e.g., (a) between the IR and inside the SOI (at the NotI site) or (b) inside the second SOI that is located 3' to the IR and 5' to the PBS (at the PacI/BamHI sites). Either way, the resulting ssDNA is specific for the target DNA sequence(s), mRNA sequence(s), or any other suitable substrate, to inhibit or change DNA or mRNA splicing mechanisms, or even to directly alter the cellular genome in a specific manner. Those skilled in the art will recognize from this disclosure that any DNA sequence having enzymatic activity will function for the intended purpose when inserted into the cassette of the present invention. A number of nucleic acid sequences with enzymatic activity have been reported in the literature, including:

sequences having RNAse activity such as the so-called "10-23" and "8-17 enzymes" (Santoro, S. W. and G. F. Joyce, supra (1997)) and other metal-dependent RNAses (Breaker, R. R. and G. F. Joyce, 1 Biol. Chem. 223-229 (1994) and Breaker, R. R. and G. F. Joyce, 2 Biol. Chem. 655-660 (1995)) and histidine-dependent RNAse (Roth, A. and R. R. Breaker, 95 Proc. Natl Acad. Sci. USA 6027-6031 (1998));

sequences having DNAse activity such as copper-dependent DNAse (Carmi, N., et al., 3 Chem. Biol. 1039-1046 (1996), Carmi, et al., supra (1997); Sen, D. and C. R. Geyer, 2 Curr. Opin. Chem. Biol. 680-687 (1998)) and the DNAses which required divalent metal ions as cofactors or hydrolyzed the substrate independently of divalent metal ions reported in Faulhammer, D. and M. Famulok (269 J. Molec. Bio. 18-203 (1997));

sequences with DNA ligase activity such as copper-dependent DNAse (Breaker, R. R., 97 Chem. Rev. 371-390 (1997)) and zinc-dependent E47 ligase (Cuenoud, B. and J. W. Szostak, 375 Nature 611-613 (1995));

sequences with DNA kinase activity such as calcium-dependent DNA kinase (Li, Y. and R. R. Breaker, 96 Proc. Natl. Acad. Sci. USA 2746-2751 (1999)); and sequences with RNA kinase activity such as calcium-dependent DNA kinase (Li, Y., supra (1999)).

Generally, it is those DNA sequences having enzymatic activity that are derived from physiological conditions that are preferred for use in the cassette comprising the expression vector that comprises one component of the composition of the present invention. Those skilled in the art will recognize that as described above, the expression vector of the present invention is not utilized solely for the purpose of producing antisense sequences in vivo, that the antisense sequence need not necessarily contain a nucleic acid sequence having catalytic activity, and that the inhibitory nucleic acid sequence could also be any of the other types of inhibitory nucleic acid sequences described above.

It may also be advantageous if the expression vector comprising the composition of the present invention contains other specialized genetic elements to facilitate identification of cells that carry the vector and/or to increase the level of expression of the set of genetic elements comprising the cassette. The specialized genetic elements may include selectable marker genes such as genes that confer to the bacteria (e.g., *E. coli*) resistance to antibiotics such as zeocin (described infra), ampicillin, chloramphenicol, kanamycin (neomycin), or tetracycline so that the vector can be transformed and amplified in a prokaryotic system.

Incorporation of the above components into the expression vector of the present invention makes available at least two convenient methods for removing predetermined vector sequences after the production of ssDNA as shown in FIG. 1. In the first method, the cassette that comprises a portion of the expression vector is reverse transcribed in the infected cell from the PBS so that the SOI between the IR comprises the loop portion of the ssDNA stem-loop intermediate that is produced when the nucleotides comprising the IR pair up to form the stem of the stem-loop vector, the stem comprising an RE site. After digestion with the appropriate RE, the loop is released as linearized, single-stranded cDNA without (and/or with minimal) flanking sequences. In the second method, the cassette is reverse transcribed from the PBS and an SOI included in the cassette 3' to the IR is likewise transcribed, but reverse transcription is terminated at the stem of the stem-loop structure formed by the pairing of the nucleotides of the IR. Either way, the resulting ssDNA is produced without (and/or with minimal) flanking sequences. If it is desired to produce ssDNA utilizing the second method, the cassette is designed so that the transcript of the cassette includes an IR that forms a stem that is more stable than the stem produced when ssDNA is produced by digestion of the stem in accordance with the first aspect of the present invention (for instance, by designing the IR so as not to include an RE site). By designing the cassette to produce an IR that forms a stem that is easily denatured in accordance with the first aspect of the invention, reverse transcription proceeds right on through the second SOI (if it is even designed into the cassette) to the SOI located between the IR. This "premature termination" of the reverse transcriptase cDNA transcript at the 3' aspect of the stem structure therefore provides a second method for limiting the intervening vector sequences contained with an in vivo-produced ssDNA. A stem that is intermediate in stability allows production of both the first and second SOIs.

It will also be evident to those skilled in the art from this description that the intact stem-loop ssDNA structure can function similarly in many applications as the linearized ssDNA form. Consequently, the cassette is also used to advantage without the restriction endonuclease gene and associated regulatory elements and/or with a sequence of interest that lacks the corresponding restriction endonuclease site.

It will also be evident to those skilled in the art from this description of the preferred embodiments of the present invention that a cassette can be made which encodes a ssDNA that has a "trimmed" stem-loop structure. The RE sites encoded in the IR flanking the SOI are designed such that the stem portion (after duplex formation) is digested with the corresponding RE so as to cut the dsDNA comprising the stem in a way that removes a portion of the stem and the associated flanking sequences, yet leaves sufficient duplex DNA that the transcript retains the above-described stem-loop structure. Such ssDNA structure may be more resistant to intracellular nucleases by retaining the "ends" of a ssDNA in double stranded form.

The cassette of the expression vector comprising the composition of the present invention is advantageously employed to deliver antisense, triplex, or any other inhibitory nucleic acid, excitatory nucleic acid, or single-stranded nucleotide using known digestion and ligation techniques to splice the particular SOI into the cassette (between inverted tandem repeats or between PBS and inverted tandem repeats). Those skilled in the art who have the benefit of this disclosure will also recognize that the above-described signals used for expression within eukaryotic cells may be modified in ways known in the art depending upon the particular host cell and sequence being targeted. For instance, a likely modification is to change the promoter so as to confer advantageous expression characteristics on the cassette in the system in which it is desired to express the SOI. As noted above, there are many promoters that may be used to advantage in connection with the expression vector of the present invention; indeed, there are so many possible promoters (and other signals), and they are so dependent on the particular target cell for which the sequence of interest has been selected, that it is impossible to list all the potential enhancers, inducible and constitutive promoter systems, and/or poly(A) tailing systems that may be preferred for a particular target cell and SOI.

The expression vector comprising the composition of the present invention is delivered to the HSV-infected cell by topical application to the affected site. Topical application is accomplished by mixing the expression vector, having a SOI incorporated therein that targeting the sequence involved in HSV replication, in a suitable vehicle for application to the affected site. The location of the affected site is an important element in formulation of the vehicle. For instance, many affected sites occur on the patient's skin, yet the skin poses a particular challenge for topical application. Skin is composed of three major components: the epidermis, the dermis and the underlying subdermal tissue. The epidermis provides the strongest protection against absorption of an exogenous substance and is composed of five layers, the stratum corneum, stratum lucidum, stratum granulosum, stratum sponsum and stratum basale. Of these five layers, the stratum corneum, which consists of flattened, cornified cells embedded in a lipid intercellular matrix, is most impermeable. To be delivered effectively to such an affected site topically, the composition of the present invention must achieve penetration of these outer layers of the skin so that the expression vector is transfected into the target HSV-infected cells.

One example of a delivery vehicle that represents a particularly preferred embodiment of the composition of the present invention because it provides transport through the outer layers of the skin is a two-part gel of the type described in U.S. Pat. No. 5,837,289, the specification of which is hereby incorporated into this specification in its entirety by this specific reference. Briefly, this patent describes a composition comprised of two so-called "penetration enhancers" and a medication capable of being administered transdermally. In a preferred embodiment described in that patent, an organogel is prepared by blending a fatty acid phospholipid emulsifying agent such as lecithin with a fatty acid or an ester thereof, such as isopropyl palmitate or isopropyl myristate, to form an organogel that is then blended with a polyoxymer such as a polyoxyalkylene polymer, and the medication is solubilized with a solvent such as water, alcohol, or other suitable solvent and mixed with the organogel and polymeric component. However, contrary to the teaching of U.S. Pat. No. 5,837,289, it has been discovered that the expression vector that comprises one component of the composition of the present invention need not be solubilized before mixing with the organogel and polymeric component to be delivered effectively to an affected site in accordance with the method of the present invention. In fact, the expression vector that comprises the composition of the present invention is quite large such that solubilization is effectively impossible in any known solvent, yet it has been discovered that the expression vector can be suspended in the blend of the organogel and the polymeric component taught by the above-incorporated patent for successful delivery to an affected site.

In a particularly preferred embodiment, the two-part gel that is utilized as a delivery vehicle for the expression vector is a PLURONIC™ (Wyandotte Chemical Co.) lecithin oranogel, or PLO, which is a combination of PLURONIC™ gel and soy lecithin. PLURONIC™ gel is a poloxamer comprised of poly(ethylene oxide)-b-poly(propyleneoxide)-b-poly(ethylene-oxide). The most common form of PLURONIC™ gel used in pharmaceutical compounding is PLURONIC™ F-127 (BASF Corporation). Lecithin is a permeation enhancer that acts as an amphoteric surfactant in the two-part gel, thus facilitating penetration of the expression vector into the dermal layer, and the concentration of lecithin in the two-part gel yields control of various bulk properties of the two-part gel such as thixotrophy, viscosity and gelation temperature. F-127 exhibits zero order kinetics. (Moore, T., et al., Experimental investigation and mathematical modeling of Pluronic F-127 gel dissolution: drug release in stirred systems, 67 [2-3] J. Controlled Release 191-202 (2000)). With these kinetics, the amount of suspended drug delivered from the gel per unit time is constant.

This preferred embodiment of the composition of the present invention is generally made up in accordance with the same general formulas as described in the above-incorporated U.S. Pat. No. 5,837,289 with the following modification. That patent discloses a formula comprised of about <1 to 20 parts by weight of a medication and about <1 to 20 parts solvent for the medication, 20 to 40 parts by weight of the first penetration enhancer (the organogel), and 40 to 70 parts by weight of the second penetration enhancer (the polyoxymer). In the present invention, the composition is comprised of a mixture of the first and second penetration enhancers in the same ratios as described in the above-incorporated patent (about 20 to about 40 parts by weight of the organogel and about 40 to about 70 parts by weight of the polyoxymer) but the expression vector comprises between about 0.01% and about 20% (by weight), and preferably between about 0.1% to 5%, of the composition The two-part gel is preferably prepared by adding the two components of the two-part gel in proportions of between about 10 and about 40 parts by weight of the organogel and between about 20 to about 70 parts by weight of the polyoxymer, in small increments while applying sheer force, for instance, with syringe techniques, hand-held rotor tool, ELECTRO MOTOR, or ointment mill, for each part of the expression vector (by weight).

By reference to specific ingredients, a preferred embodiment of the two-part gel will now be described. Between about 4 and about 8 parts (by weight) of isopropyl palmitate are placed in a beaker or other suitable container, and between about 4 and about 8 parts of soya granular lecithin and between about 0.05 and about 0.5 parts of sorbic acid are dispersed in the beaker without shaking (the lecithin dissolves in time). A vessel is then calibrated to between about 40 ml and about 60 ml and between about 8 and about 12 parts of a polyoxymer such as CARBOPOL™ or PLURONIC™ (Wyandotte Chemical Co.) are placed in the calibrated vessel. Cold water is added to bring total volume to between about 40 and about 60 ml and the vessel is shaken before storing at normal refrigeration temperatures for long enough for the polyoxymer to dissolve (overnight). To prepare the two-part gel, about 20% (by volume) of the prepared lecithin and about 80% (by volume) of the polyoxymer gel are withdrawn into syringes and the two mixtures are transferred from one syringe to another by using a LUER LOK™-to-LUER LOK™ connector until uniform.

The desired plasmid containing the calling sequence of interest, designated as the active component, is dissolved or dispersed in sterile water. The active component with a final concentration of 0.1%, not to exceed 10% of the final volume, is then added to 2.2 ml of Lecithin/Isopropyl Palmitate solution that has been placed in a 10 cc syringe. The mixture is vortexed. Pluronic F-127, 20% is added to a second syringe to q.s. to 10 ml. Use of the syringe to syringe technique for mixing will encourage micelle formation.

In a second formulation, the plasmid dermatological preparation is prepared as follows. Salicylic acid USP, 2 gm, is mixed with vitamin E acetate (125 U/ml) 2 ml, q.s. to 100 gm with Base PCCA Cosmetic HRT (Professional Compounding Centers of America, Inc., Houston, Tex.). The plasmid with the sequence of interest, designated as the active ingredient, is diluted in sterile water. The plasmid with the sequence of interest is then q.s to 10 ml in the Base PCCA Cosmetic HRT to a final concentration of 0.01% weight of plasmid to volume and is mixed using the syringe to syringe technique.

In a second embodiment, network poly(amino ester) (n-PAE) and other modified polyethylenimine (PEI) lipopolymers as described by T. M. Klibanov (Enhancing polyethylenimine's delivery of plasmid DNA into mammalian cells, 99 Proc. Natl Acad. Sci. USA 14640-5 (2002)), C. Rudolph, et al. (Nonviral gene delivery to the lung with copolymer-protected and transferrin-modified polyethylenimine, 1573 Biochim. Biophys. Acta 75 (2002)), Y. B. Lim, et al. (Biodegradable, Endosome Disruptive, and Cationic Network-type Polymer as a Highly Efficient and Nontoxic Gene Delivery Carrier, 13 Bioconjug. Chem. 952-7 (2002)), A. Kichler, et al. (Intranasal gene delivery with a polyethylenimine-PEG conjugate, 81 J. Control Release 379-88 (2002)), P. Lampela, et al. (The use of low-molecular-weight PEIs as gene carriers in the monkey fibroblastoma and rabbit smooth muscle cell cultures, 4 J. Gene Med. 205-14 (2002)), W. S. Manuel, et al. (Transfection by polyethyleneimine-coated microspheres, 9 J. Drug Target 15-22 (2001)), and W. T. Godbey, et al. (Size matters: molecular weight affects the efficiency of poly(ethylenimine) as a gene delivery vehicle, 45 J. Biomed Mater. Res. 268-75 (1999)) are used to advantage as a vehicle for delivery of the expression vector described herein. Alternatively, graft copolymers of PEI and PLURONIC gel as described by C. L. Gebhardt, et al. (Design and formulation of polyplexes based on pluronic-polyethyleneimine conjugates for gene transfer, 1 Bioconjug. Chem. 937-44 (2002) and P. Lemieux, et al. (Block and graft copolymers and NanoGel copolymer networks for DNA delivery into cell, 8 J. Drug Target 91-105 (2000)) are used to advantage as the delivery vehicle of the composition of the present invention.

In yet another embodiment, the above-described expression vector is delivered to an affected site in a cationic block copolymer of the type described in A. Caputo, et al. (Micellar-type complexes of tailor-made synthetic block copolymers containing the HIV-1 tat DNA for vaccine application, 20 Vaccine 2303-2317 (2002)), the entirety of which is hereby incorporated herein by this specific reference thereto. Other types of micelles such as polyion complex (PIC) micelles as described by M. Harada-Shiba, et al. (Polyion complex micelles as vectors in gene therapy-pharmacokinetics and in vivo gene transfer, 9 Gene Ther. 407-14 (2002)) are also utilized to advantage as the delivery vehicle in the composition of the present invention. Similarly, the expression vector is delivered to an affected site in micelles formed of the water-soluble lipopolymers described in D. A. Wang, et al. (Novel Branched Poly(Ethylenimine)-Cholesterol Water-Soluble Lipopolymers for Gene Delivery, 3 Biomacromolecules 1197-1207 (2002)). All of the references cited in these two paragraphs are hereby incorporated herein in their entireties by this specific reference thereto, and the expression vector is mixed with the vehicle in the proportions and in accordance with the methods set out in the thus-incorporated references.

In another embodiment, the delivery vehicle of the present invention also includes an ingredient such as an antibiotic, analgesic, and/or anesthetic for treatment of symptoms at the affected site. For instance, formulations of the composition of the present invention for topical application at the site of a viral eruption might include an anesthetic for relief of pain such as lidocaine; alternatively, if the affected site is also the site of a bacterial infection, the composition of the present invention may include an antibiotic such as kanamycin or any of the many known antibiotics that are advantageously applied topically.

EXAMPLES

Except where otherwise indicated, standard techniques as described by Sambrook, et al. (1989) (J. Sambrook, et al., Molecular Cloning: A Laboratory Manual (2nd Ed.), Cold Spring Harbor Press (1989), hereinafter referred to as "Maniatis, et al. (1989)") and Ausubel, et al. (1987) (F. M. Ausubel, et al., Current Protocols in Molecular Biology, New York: John Wiley & Sons (1987)), both of which are hereby incorporated in their entirety by this specific reference thereto, were utilized in the examples set out below. It should be understood that other methods of production of ssDNA, both by natural processes and by designed artificial methods using different enzyme products or systems, may also be utilized in connection with the method of the present invention and that the examples set out herein are set out for purposes of exemplification and are not intended to limit the scope of this disclosure or the invention described herein.

Construction of plasmids was as described in co-pending U.S. application Ser. No. 10/136,218, filed May 1, 2002, which application is hereby incorporated into this specification in its entirety by this specific reference thereto. Specifically, expression vectors constructed in accordance with the teachings of the present invention are the pssXE (for cell culture studies) and pssXV (for animal testing) plasmids shown in FIGS. 3 and 4. To make pssXE and pssXV, the pssXB and pssXD plasmids described in the above-incorporated co-pending application were double-digested with NheI and XhoI. The DNA fragment digested from pssXD (containing RT, PBS, and other component necessary for synthesis of ssDNA) was subcloned into the vector double digested from pssXB with the same enzymes that contains a CMV promoter. A multiple cloning site (MCS) was created in order to facilitate subcloning the sequence of interest into the plasmid by annealing and subcloning the sequences

```
5'-E/S/P/P-LINKER                              SEQ ID NO:2
(5'-TCGAGCGGCCAGGGGTCTCCCGATCCCGGAC
GAGCCCCCAAAGAATTC-CGCGGCTGCAGTTAAT-3') and 3'-E/S/P/P-LINKER                              SEQ ID NO:3
(5'-TAACTGCAGCCGCG-GAATTCTTTGGGGGCTC
GTCCGGGATCGGGAGACCCCTGGCCGC-3')
``` into PacI and XhoI sites of pssXD plasmid to create four new restriction enzyme recognition sites, EcoRI, SacII, PstI and PacI.

```
                                               SEQ ID NO:4
5'-CCCTTATACGATTTTCGCGCATATCGTATCCCGCCG-3'

SEQ ID NO:5
5'-GGGCCCATACGATTTTTTTTTATCGTATGGGCCC-3'

SEQ ID NO:6
TCCGCCAGGCTACGTACAACGATTCCAGG-3'

SEQ ID NO:7
CGGCGTAGGCTAGCTACAACGAGTCCTGG-3'

SEQ ID NO:8
AGAAACAGGCTAGCTACAACGAGTCCGTC-3'

SEQ ID NO:9
ATCGCCAGGCTAGCTACAACGAACGTCCG-3'
```

The following sequences were cloned into the PacI and EcoRI sites of pssXE:

SEQ ID NO: 4 binds to the ICP4 transcription factor that regulates expression of many HSV genes by binding to their promoter regions and works in competitive fashion to prevent ICP4 from interacting with gene promoters in both HSV1 and HSV2. SEQ ID NO: 5 is a control sequence, and both SEQ ID NOS: 4 and 5 were cloned in pssXE and sequences confirmed by automatic sequencing using the BGHRev primer.

SEQ ID NOS: 6 and 7 were designed to include DNA enzymes that target a protein, ICP47-1, from HSV-1, SEQ ID NO: 6 binding to the ICP-47 mRNA sequence at the position between 12nt and 26nt, and SEQ ID NO: 7 binding to the sequence at the position between 56nt and 70nt. Similarly, SEQ ID NOS: 8 and 9 were designed to include DNA enzymes that target a protein ICP47-2 from HSV-2, SEQ ID NO: 8 binding to the ICP-47 mRNA sequence at the position between 21nt and 35nt and SEQ ID NO: 9 binding to the mRNA sequence at the position between 58nt and 72nt. Again, sequences were confirmed by sequencing using the BGHRev primer.

The experiments described above demonstrate the use of an expression vector for production of ssDNA in HSV-infected cells by multiple stepwise reactions using eukaryotic RT reactions and various cDNA priming reactions that alter gene function of the genes involved in replication of HSV and protection of HSV from the host's immune system. Those skilled in the art will recognize that the present invention is not limited to the specific embodiments of such expression vectors described herein. It will be recognized, for instance, that many nucleic acid sequences may be utilized depending upon the specific target sequence and/or mode of inhibitory action of the SOI. Similarly, the SOI may be located in either or both of the two positions, e.g., between the IR and/or between the PBS and the 340 aspect of the IR. Likewise, the SOI may or may not include a DNA enzyme sequence depending upon the particular target sequence and/or mode of action of the SOI and/or the DNA enzyme sequence. By way of example, and not limitation, the following inhibitory nucleic acid sequences are known in the art and may be utilized as the SOI to alter expression of one or more genes involved in proliferation of HSV when incorporated into an expression vector constructed in accordance with the teachings of the present invention and applied topically to an affected site:

Sequences that act as antisense oligonucleotides to bind to one or more target sequences, or to the mRNA molecules transcribed from the target sequences, of HSV other than ICP4 and ICP47 such as ICP0, ICP22, and ICP27;

Sequences that inhibit expression of transcription regulatory factors such as described in U.S. Pat. No. 5,795,721;

Oligonucleotides for controlling expression of viral structural proteins;

Sequences that act as triplex forming oligonucleotides (TFOs) at one or more target sequences of the host cell after integration of the HSV genome, for instance, to down regulate the sites from which the host cell produces ICP4, ICP47, ICP0, ICP22, and ICP27 or other proteins involved in viral proliferation and/or protection of the virus from the host immune system;

Oligonucleotides specifically hybridizable with a translation initiation site, coding region or 5' untranslated region of HSV. The oligonucleotides are designed to be specifically hybridizable with DNA, or preferably, RNA from one of the species herpes simplex virus type 1 (HSV-1), herpes simplex virus type (HSV-2), human herpes virus 6, Epstein Barr virus (EBV), or varicella zoster virus (VZV). Such oligonucleotides are conveniently and desirably presented as a pharmaceutical composition in a pharmaceutically acceptable carrier as described in U.S. Pat. No. 5,514,577. Persons skilled in the art who have the benefit of this disclosure will recognize that the particular genes described for HSV find counterparts in other viruses. Thus each of herpes simplex virus type 2, human herpes virus type 6, EBV, and VZV have genes that code for proteins having similar functions. Accordingly, the present invention contemplates ODN-mediated therapy in which the ODNs are directed to any of the foregoing viruses; and/or Protein-binding oligonucleotides (aptamers) that specifically bind target molecules such as the proteins comprising the HSV protein coat, thereby preventing assembly of the protein coat.

This list is not intended to be all-inclusive. It is envisioned that expression vectors can be constructed in accordance with the present invention that are capable of transfection into any HSV-infected cell for producing a sequence that can target any, or at least a wide variety, of genes and/or the control functions for the genes involved in HSV replication to alter the function of the target gene(s).

Although described with reference to the figures and specific examples set out herein, those skilled in the art will recognize that certain changes can be made to the specific elements set out herein without changing the manner in which those elements function to achieve their intended respective results. For instance, the cassette described herein is described as comprising three genetic elements, a sequence of interest, a primer binding sequence, and a tandem inverted repeat, and when transfected into a target cell with a reverse transcriptase gene under control of a suitable promoter, produces the inhibitory nucleic acid sequence described herein. However, those skilled in the art will recognize that, for instance, the reverse transcriptase gene of the cassette can be replaced with other reverse transcriptase genes (the reverse transcriptase gene from human immunodeficiency virus was one such gene which was noted above) and that promoters other than the CMV promoter described herein may be used to advantage. As noted above, the stem-loop intermediate that is formed may or may not include a restriction endonuclease site and its susceptibility to denaturation is manipulated to advantage depending upon the particular sequence of interest that is intended to be produced from that intermediate. All such changes, and others that will be made clear to those skilled in the art by this description modifications which do not depart from the spirit of the present invention, are intended to fall within the scope of the following claims.

What is claimed is:

1. A topical composition for the treatment of HSV-related pathologies comprising:
   (a) a single-stranded DNA (ssDNA) expression vector, other than plasmids pssXE and pssXV, having a gene encoding for a reverse transcriptase (RT) and a ssDNA expression cassette comprising in 5' to 3' order:
      (i) a cytomegalovirus (CMV) or Rous Sarcoma virus (RSV) promoter sequence,
      (ii) an inverted tandem repeat (IR) sequence,
      (iii) a sequence of interest comprising SEQ ID NO: 4, and
      (iv) a mammalian reverse transcriptase primer binding site (PBS) sequence; and
   (b) a topical ointment or cream;
   wherein the ssDNA so produced has minimal flanking sequence.

2. The composition of claim 1 in which the RT is mouse Maloney reverse transcriptase (MoMuLV-RT).

3. The composition of claim 1 in which the IR sequence comprises SEQ ID NO: 10.

4. The composition of claim 1 in which the PBS site on the transcribed mRNA promotes binding of the MoMuLV-RT with an appropriate tRNA.

5. The composition of claim 1 additionally comprising an antibiotic.

6. The composition of claim 1 additionally comprising either or both of an anaesthetic or analgesic.

7. The composition of claim 1 additionally comprising one or more of vitamins A, D, and E.

8. The composition of claim 1 wherein said ointment or cream comprises a two-part gel, a Base PCCA Cosmetic HRT, or PLO.

9. A method for treatment of HSV-related pathologies involving the application of a composition comprising an in vivo ssDNA expression vector, other than plasmids pssXE and pssXV, carrying SEQ ID NO: 4, to an affected site.

10. The method of claim 9 wherein the composition includes a topical ointment, a topical cream, or a topical spray.

11. A ssDNA expression vector comprising a gene encoding for a reverse transcriptase and a ssDNA expression cassette comprising in 5' to 3' order:
   (i) a cytomegalovirus (CMV) or Rous Sarcoma virus (RSV) promoter sequence,
   (ii) an inverted tandem repeat (IR) sequence comprising SEQ ID NO: 10,
   (iii) a convenient cloning site, and
   (iv) a mammalian reverse transcriptase primer binding site (PBS), wherein the ssDNA so produced has minimal flanking sequence.

12. The ssDNA expression vector of claim 11 having the genetic composition of plasmid pssXV.

13. The composition of claim 1 in which the sequence of interest comprises one or more sequences having SEQ ID NO: 4.

\* \* \* \* \*

SEQUENCE LISTING

<160> NUMBER OF SEQ ID NOS: 10

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Consensus
      binding site
<220> FEATURE:
<221> NAME/KEY: modified_base
<222> LOCATION: (7)..(8)
<223> OTHER INFORMATION: a, t, c or g
<220> FEATURE:
<221> NAME/KEY: modified_base
<222> LOCATION: (10)
<223> OTHER INFORMATION: a, t, c or g

<400> SEQUENCE: 1
rtcgtcnnyn ysg                                                        13

<210> SEQ ID NO 2
<211> LENGTH: 64
<212> TYPE: DNA
<213> ORGANISM: Artificial Sequence
<220> FEATURE:
<223> OTHER INFORMATION: Description of Artificial Sequence: Linker
      oligonucleotide

<400> SEQUENCE: 2
tcgagcggcc aggggtctcc cgatcccgga cgagccccca aagaattccg cggctgcagt      60
taat                                                                  64

<210> SEQ ID NO 3
<211> LENGTH: 58
<212> TYPE: DNA
<213> ORGANISM: Artificial Sequence
<220> FEATURE:
<223> OTHER INFORMATION: Description of Artificial Sequence: Linker
      oligonucleotide

<400> SEQUENCE: 3
taactgcagc cgcggaattc tttgggggct cgtccgggat cgggagaccc ctggccgc        58

<210> SEQ ID NO 4
<211> LENGTH: 36
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 4
cccttatacg attttcgcgc atatcgtatc ccgccg                              36

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gggcccatac gattttttt ttatcgtatg ggccc                                35

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tccgccaggc tacgtacaac gattccagg                                      29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cggcgtaggc tagctacaac gagtcctgg                                      29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agaaacaggc tagctacaac gagtccgtc                                      29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atcgccaggc tagctacaac gaacgtccg                                      29

<210> SEQ ID NO 10
<211> LENGTH: 29
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 10
ggtcggcggc cttgaagagc ggccgcact                                            29
```